United States Patent
Haley

(10) Patent No.: US 9,789,061 B2
(45) Date of Patent: Oct. 17, 2017

(54) ACACIA GUM ADHESIVE WITH CALCIUM CARBONATE FOR ORAL ADHERING DISCS

(71) Applicant: ORAHEALTH CORPORATION, Bellevue, WA (US)

(72) Inventor: Jeffrey Haley, Mercer Island, WA (US)

(73) Assignee: OraHealth Corp., Seattle, WA (US)

( * ) Notice: Subject to any disclaimer, the term of this patent is extended or adjusted under 35 U.S.C. 154(b) by 0 days.

(21) Appl. No.: 14/379,692

(22) PCT Filed: Feb. 18, 2013

(86) PCT No.: PCT/US2013/026609
§ 371 (c)(1),
(2) Date: Aug. 19, 2014

(87) PCT Pub. No.: WO2013/123487
PCT Pub. Date: Aug. 22, 2013

(65) Prior Publication Data
US 2015/0272871 A1    Oct. 1, 2015

(51) Int. Cl.
| | |
|---|---|
| *A61K 9/20* | (2006.01) |
| *A61K 9/14* | (2006.01) |
| *A61K 9/00* | (2006.01) |
| *A61K 47/36* | (2006.01) |

(52) U.S. Cl.
CPC ............ *A61K 9/006* (2013.01); *A61K 9/2009* (2013.01); *A61K 9/2068* (2013.01); *A61K 9/2086* (2013.01); *A61K 9/2095* (2013.01); *A61K 47/36* (2013.01)

(58) Field of Classification Search
CPC ...... A61K 9/0056; A61K 9/20; A61K 9/2086; A61K 9/205; A61K 9/2095
See application file for complete search history.

(56) References Cited

U.S. PATENT DOCUMENTS

| | | | | |
|---|---|---|---|---|
| 5,302,628 A | * | 4/1994 | Lim | A61K 6/0026 433/180 |
| 2007/0274927 A1 | * | 11/2007 | Haley | A61K 9/0056 424/48 |
| 2009/0169489 A1 | * | 7/2009 | Haley | A61K 9/0056 424/48 |

* cited by examiner

Primary Examiner — Tracy Liu

(57) ABSTRACT

This invention is directed to a superior adhesive for oral adhering discs or troches. The adhesive is at least 80% acacia gum mixed with calcium carbonate so that, as the acacia gum is combined with water, it does not yield a pH lower than 5.5. The preferred ratio of acacia gum to calcium carbonate is within the range 15:1 to 50:1.

5 Claims, 1 Drawing Sheet

| Ratio Acacia Gum to $CaCO_3$ | pH |
|---|---|
| 19 : 1 | 6.4 |
| 20 : 1 | 6.3 |
| 26 : 1 | 6.2 |
| 33 : 1 | 6.1 |
| 41 : 1 | 6.1 |

ACACIA GUM ADHESIVE WITH CALCIUM CARBONATE FOR ORAL ADHERING DISCS

This application is a continuation of PCT US 2013 026609 filed Feb. 18, 2013 and claims priority from U.S. 61/600,659 filed Feb. 19, 2012.

BACKGROUND

Oral adhering discs, also called adhering troches, are known for time release of ingredients into saliva in the mouth or into the mucosa to which the disc is adhered or into mucosa that the disc touches while the disc is adhered to teeth or gums. Some oral adhering discs have two layers, a thin adhesive layer and a thicker, slowly dissolving ingredient release layer. Many synthetic hydrophilic compounds are known for use as the adhesive layer, such as poly-acrylic acid, carbomer, carbopol, and povidone. An effective natural compound, in sufficient concentration, is acacia gum, also known as gum arabic. As it dissolves in saliva, acacia gum adhesive is acidic, producing a local pH below 5.5, which is more acidic than desirable for contact with teeth.

Of course, the adhering objects need not be disc shaped. They may be squarish or oval or oblong or any other shape that is roughly flat at least on one side. A generic term that includes all such shapes is "adhering troche" (which a term for an object held in the mouth to achieve an effect).

SUMMARY OF THE INVENTION

The present invention provides a natural muco-adhesive composition that is effective for adhering troches and is less acidic than pure acacia gum made by mixing an alkalizer (base) with the acacia gum.

In one aspect, the invention is an adhering troche having two sides that, when held in a human mouth, adheres and remains in the mouth as a single item that does not smear or break apart, made by a process comprising, (a) forming a first layer, roughly disc-shaped and having a roughly flat side at least 5 mm in two dimensions, comprising an ingredient to be released into saliva and/or mucosa; (b) forming a second, adhesive layer, roughly disc-shaped and having a roughly flat side at least 5 mm in two dimensions, comprising at least 80% acacia gum mixed with a sufficient quantity of alkalizer that the pH of the mixture is 5.5 or higher when dissolved in 10 parts water; and (c) adhering the layers to each other, side to side, such that one entire side of the resulting troche is adhesive and the other entire side of the resulting troche is not adhesive.

The particles of the alkalizer may be adhered to particles of the acacia gum by a wet granulation process and the resulting combined particles may then be pressed into a bi-layer troche with a bi-layer tablet press.

The particles of the alkalizer may be dry mixed with particles of the acacia gum and the resulting mixture then pressed into a bi-layer troche with a bi-layer tablet press.

The particles of the alkalizer may be wet mixed with particles of the acacia gum and the resulting mixture then dried into granules and the granules then pressed into a bi-layer troche with a bi-layer tablet press.

The particles of the alkalizer may be wet mixed with particles of the acacia gum and the resulting mixture then spread into a layer on a sheet and the sheet then cut into a bi-layer troche.

The particles of the alkalizer may be mixed with particles of the acacia gum and the resulting mixture then pressure extruded to make a bi-layer sheet which may be cut into troches. These adhering troches may be made by hot pressing the sheet with dies that hot-squish the sheet to separate it into individual troches and then cooling.

The adhesive layer adheres to a roof of a mouth of a human strongly enough to hold triple the weight of the troche against force of gravity and strongly enough to hold the weight of the troche plus an additional 680 milligrams against force of gravity.

The preferred alkalizer is calcium carbonate.

In another aspect, the invention is an adhering troche having two sides that, when held in a human mouth, adheres and remains in the mouth as a single item that does not smear or break apart, comprising (a) a first layer, roughly disc-shaped and having a roughly flat side at least 5 mm in two dimensions, comprising an ingredient to be released into saliva or mucosa; (b) a second, adhesive layer, roughly disc-shaped and having a roughly flat side at least 5 mm in two dimensions, comprising at least 80% acacia gum mixed with a sufficient quantity of alkalizer that the pH of the mixture is 5.5 or higher when dissolved in 10 parts water; and (c) the layers being adhered to each other, side to side, such that one entire side of the resulting troche is adhesive and the other entire side of the resulting troche is not adhesive.

In another aspect, the invention is an adhering troche, at least 5 mm in two dimensions, that, when held in a human mouth, adheres and remains in the mouth as a single item that does not smear or break apart, comprising, (a) a first layer comprising an ingredient to be released into saliva; and (b) a second, adhesive layer comprising at least 80% acacia gum mixed with a sufficient quantity of alkalizer that the pH of the mixture 5.5 or higher dissolved in 10 parts water.

DESCRIPTION OF THE DRAWING

FIG. 1 presents a table of experimental embodiments of the invention made with mixtures of acacia gum with calcium carbonate.

DETAILED DESCRIPTION OF THE INVENTION

In preferred embodiments, the acacia gum is pressed from a dry powder into one layer of a bi-layer disc with a bi-layer tablet press as taught by U.S. patent application Ser. No. 11/800,381 filed May 4, 2007 by the same inventor which is incorporated by reference. The alkalizer (base) may be mixed as a dry powder with the acacia gum powder, or it may be granulated with the acacia gum powder in a wet-granulation process or a dry granulation process.

In an alternative embodiment, the acacia gum may be mixed with a liquid such as water or alcohol to form a thick paste which is then spread onto a sheet, such as a sheet of a composition including an ingredient to be delivered. The sheet may be dried and then cut into discs or first cut into discs and then dried. The alkalizer is mixed into the paste before spreading on the sheet.

In another alternative embodiment, the acacia gum may be mixed with the alkalizer and then pressure extruded to form a sheet from which discs are cut.

The alkalizer (base) is added in the least amount that achieves the desired neutralization, to keep the acacia gum as concentrated as possible to maintain maximum adhesive effectiveness.

To be an effective adhesive layer for a thin oral adhering disc weighing less than 340 milligrams, the adhesive layer should adhere to a roof of a mouth of a human strongly enough to hold triple the weight of the disc against force of gravity.

To be an effective adhesive layer for a thick oral adhering disc weighing more than 340 milligrams, the adhesive layer should adhere to a roof of a mouth of a human strongly enough to hold the weight of the disc plus an additional 680 milligrams against force of gravity.

In the case of acacia gum, for adequate adhesive strength, the acacia gum should be at least 80%, allowing up to 20% alkalizer or other additives.

Any known alkalizer that allows the finished product to remain adequately shelf stable may be used.

The alkalizer may be mixed with wet acacia gum, neutralizing the acacia gum before it is granulated, dried, and tablet pressed or spread as a paste. In this method, a strong alkalizer, such as KOH (potassium hydroxide) or sodium hydroxide, may be used and titrated to a pH between 5.5 and 8.0, preferably 6.0-7.0.

For ease of manufacturing finished discs with a bi-layer tablet press, it is preferred to obtain the acacia gum as a powder, then mix in a powdered alkalizer, and then use the mixture directly in a tablet press. Any alkalizer that can be obtained as a powder and will remain shelf stable when mixed with powdered acacia gum can be used. Examples include calcium carbonate, magnesium carbonate, sodium bicarbonate, potassium bicarbonate, sodium carbonate, magnesium hydroxide, aluminum hydroxide, and $C_7H_5BiO_4$.

Effective ratios of calcium carbonate to acacia gum range down to 1:50. A preferred formulation uses fine powder calcium carbonate in a ratio with acacia gum calcium within the range 1:15 to 1:50. The presently most preferred ratio is 1 to 40. Tests show that this mixture keeps the pH above 5.5 as the mixture dissolves in distilled water. Measured pH's range from 6.0 to 6.4. If the amount of calcium carbonate is increased, the pH can be as high as 7.0 but this is not optimal as the adhesiveness of the acacia gum is somewhat reduced.

The powders may be pressed into a disc shaped tablet. Such a tablet is preferably 9-16 mm in diameter and 70-800 milligrams in weight. The upper punch should be shaped for good contact with a surface in the mouth, usually essentially flat, sometimes with a bump in the center to create a dimple in the disc surface, sometimes cupped to give a domed surface such as for adhesion to the roof of the mouth. The lower punch may be cupped to provide a domed outer surface on a thick disc, or it may be nearly flat for a thin disc.

EXAMPLES

The following examples are presented by way of illustration and not by way of limitation on the scope of the invention. To determine appropriate ratios, dry acacia gum was mixed with 10 parts water and the resulting pH was measured at 4.4. The pH was also measured for the following mixtures:

Example 1

| Water | Acacia gum | CaCO$_3$ | Ratio AG/CaCO$_3$ | pH |
|---|---|---|---|---|
| 40 | 4.4 | 0.6 | 7.3:1 | >7.0 |
| 108.2 | 4.8 | 0.6 | 8:1 | >7.0 |
| 108.2 | 5.6 | 0.6 | 9.3:1 | 6.7 |
| 108.2 | 8.4 | 0.6 | 14:1 | 6.5 |
| 6.6 | 3.3 | .22 | 15:1 | 6.45 |
| 7.0 | 3.0 | .16 | 19:1 | 6.4 |
| 12.3 | 4.0 | .20 | 20:1 | 6.35 |
| 9.46 | 5.5 | .27 | 20:1 | 6.25 |
| 7.0 | 3.0 | .12 | 25:1 | 6.1 |
| 15.8 | 7.32 | .28 | 26:1 | 6.2 |
| 15.8 | 7.32 | .22 | 33:1 | 6.1 |
| 13.5 | 6.59 | .18 | 37:1 | 6.3 |
| 13.5 | 6.59 | .16 | 41:1 | 6.1 |

Example 2

| Water | Acacia gum | NaHCO3 | Ratio AG/alkali | pH |
|---|---|---|---|---|
| 6.3 | 1.8 | .28 | 6.4:1 | 8.04 |

Example 3

| Water | Acacia gum | K$_2$HPO$_4$ | Ratio AG/alkali | pH |
|---|---|---|---|---|
| 6.3 | 1.8 | .28 | 6.4:1 | 8.04 |
| 4.2 | 3.2 | .16 | 20:1 | 5.8 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

I claim:

1. A method of making an adhering troche having two sides that, when held in a human mouth, adheres and remains in the mouth as a single item that does not smear or break apart, comprising,
    (a) pressing a powder comprising an ingredient to be released into saliva to form a layer, roughly disc-shaped and having a roughly flat side at least 5 mm in two dimensions;
    (b) pressing granules of powder where a plurality of the granules each contains particles of both acacia gum and calcium carbonate that are granulated together to form an adhesive layer, roughly disc-shaped and having a roughly flat side at least 5 mm in two dimensions,
    wherein the granules of powder comprises at least 80% acacia gum mixed with a sufficient quantity of calcium carbonate such that the pH of the mixture is 5.5 or higher when dissolved in 10 parts water; and
    wherein the two layers are pressed together leaving one side of each layer exposed such that one side of the resulting troche is adhesive and the other side of the resulting troche is not adhesive.

2. The method of claim 1, wherein the granules of powder are made by wet mixing particles of calcium carbonate with particles of acacia gum and the resulting mixture is then dried into granules.

3. The method of claim 1 wherein the adhesive layer adheres to a roof of a mouth of a human strongly enough to hold triple the weight of the troche against force of gravity.

4. The method of claim 1 wherein the adhesive layer adheres to a roof of a mouth of a human strongly enough to hold the weight of the troche plus an additional 680 milligrams against force of gravity.

5. The method of claim 1, wherein the pressing is performed with a bi-layer tablet press.

\* \* \* \* \*